| United States Patent [19] | [11] | 4,170,644 |
|---|---|---|
| Gustafson et al. | [45] | Oct. 9, 1979 |

[54] **METHOD FOR THE CONTROL OF *BORDETELLA BRONCHISEPTICA* IN SWINE WITH ANTIBIOTIC BM123γ**

[75] Inventors: Richard H. Gustafson, Lawrenceville; Gordon A. Kemp, Princeton, both of N.J.

[73] Assignee: American Cyanamid Company, Stamford, Conn.

[21] Appl. No.: 925,663

[22] Filed: Jul. 17, 1978

[51] Int. Cl.² ............................................. A61K 31/71
[52] U.S. Cl. ................................................... 424/181
[58] Field of Search ......................................... 424/181

[56] References Cited

U.S. PATENT DOCUMENTS

| 4,007,167 | 2/1977 | Martin et al. | 424/181 |
| 4,018,972 | 4/1977 | Hlavka | 424/181 |
| 4,048,431 | 9/1977 | Hlavka et al. | 424/181 |

*Primary Examiner*—Sam Rosen
*Attorney, Agent, or Firm*—H. G. Jackson

[57] ABSTRACT

The invention is a method for the control of *Bordetella bronchiseptica,* the bacterial organism causing atrophic rhinitis in swine, comprising administering orally, or parenterally a pharmaceutically effective amount of Antibiotic BM123γ in, or with the feed of the host animal. The present invention further relates to antibiotic BM123γ and certain derivatives thereof, useful for the control of *B. bronchiseptica*.

7 Claims, No Drawings

METHOD FOR THE CONTROL OF *BORDETELLA BRONCHISEPTICA* IN SWINE WITH ANTIBIOTIC BM123γ

The invention is a method for the control of and protection against *Bordetella bronchiseptica*, one of the causative bacterial organisms of atrophic rhinitis of swine, comprising administering orally to swine, and especially to piglets, in, or with their feed a pharmaceutically effective amount of an antibiotic BM123γ and pharmaceutically acceptable salts thereof daily, for a period of time needed to achieve the control and/or protection.

Atrophic rhinitis is a disease of the nasal cavities of swine, also referred to as turbinate atrophy. This disease not only results in stunting and atrophy of the delicate nasal turbinate bones of swine, but also retards the growth rate of the animals affected. This disease results from the infection of the nasal cavities of swine, and especially piglets with certain bacterial organisms including *Bordetella bronchiseptica*.

Unfortunately, atrophic rhinitis is quite prevalent among swine, and the causative bacterial organisms can be found in mature animals, including gilts, and sows, and boars of breeding herds. Thus the problem of baby pigs being exposed to *B. bronchiseptica* which causes atrophic rhinitis is quite acute, and consequently prophylaxis and control of the disease is highly desired.

As stated above, we find that *Bordetella bronchiseptica*, the bacterial organism of atrophic rhinitis can be controlled by the novel method of the present invention comprising administering to swine, and especially piglets, orally, or parenterally a pharmaceutically effective amount of antibiotic BM123γ of the structure represented by formula (I):

$$R-\left\langle\phantom{x}\right\rangle-\overset{trans}{CH=CH}-\overset{O}{\underset{\|}{C}}-NH-(CH_2)_3-$$

$$-NH-(CH_2)_4-NH-R_1$$

wherein $R_1$ is hydrogen, alkyl $C_1$-$C_{10}$, alkyl $C_2$-$C_6$ monosubstituted with halo or hydroxy; and wherein R is a moiety of:

[chemical structure]

or

[chemical structure]

and mixtures thereof; and pharmaceutically acceptable salts thereof.

A preferred group of compounds represented by formula (I) are those, wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl or 1-methyl-2-hydroxypropyl.

The most preferred antibiotic of formula (I) is the compound wherein $R_1$ is isopropyl. Hereinafter, this compound is also referred to as isopropyl BM123γ.

Pharmaceutically acceptable acids, which may be used to prepare salts of the above antibiotics, are, among others, hydrochloric acid, sulfuric acid, phosphoric acid, citric acid, tartaric acid, and the like.

The preparation and properties of the above BM123γ antibiotics are set forth in U.S. Pat. Nos. 4,007,167 (1977), No. 4,018,972 (1977) and No. 4,048,431 (1977).

By the novel method of the present invention, an antibiotic of formula (I), preferably isopropyl BM123γ is administered for prophylaxis and/or control of *Bordetella bronchiseptica* to the host animal orally, in, or with their feed, in amounts of from 1 to 100 ppm and preferably 5 to 25 ppm by weight of feed daily, for a period of time required to provide protection to the animals, or until control of *B. bronchiseptica* is achieved.

In practice, the active material will generally be formulated as a premix and/or animal feed supplement which is admixed with a nutritionally balanced feed, or is added to the feed as a top dressing, or the like.

Premixes may be prepared by blending about 70 to 99% by weight of rice flour, ground rice hulls, ground corn and the like, with about 30 to 1% by weight of an antibiotic BM123γ of formula (I) and pharmaceutically acceptable salts thereof.

Should it be desired, the antibiotic BM123γ and salts thereof may also be administered to the swine in their drinking water.

Alternatively, pills, tablets, boluses and the like, containing the above antibiotic and suitable for oral administration, may be prepared by known and pharmaceutically acceptable methods.

We however, prefer oral administration of the antibiotic(s) to swine in, or with their feed.

The following, non-limiting Example serves to further illustrate the invention.

EXAMPLE 1

In vitro evaluation of the efficacy of isopropyl BM123γ for the control of *Bordetella bronchiseptica*.

Minimal inhibitory concentrations (MIC) are determined for *Bordetella bronchiseptica* strains, isolated from swine turbinate samples obtained from swine exhibiting symptoms of atrophic rhinitis.

Method

Serial, two-fold dilutions of isopropyl BM123γ are prepared in trypticase soy broth. To each tube containing 5 ml of broth is added 0.1 ml of a $10^{-3}$ dilution of bacterial inoculum, adjusted prior to dilution to 44% transmission at 645 mu. An inoculated broth, containing no dr